(12) United States Patent
Schmidt

(10) Patent No.: US 10,384,079 B2
(45) Date of Patent: Aug. 20, 2019

(54) METHOD AND COMPUTER USING CONTOUR DETERMINATION FOR CONFIGURING A RADIOTHERAPY APPARATUS

(71) Applicant: Siemens Healthcare GmbH, Erlangen (DE)

(72) Inventor: Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 435 days.

(21) Appl. No.: 15/356,018

(22) Filed: Nov. 18, 2016

(65) Prior Publication Data

US 2017/0143993 A1 May 25, 2017

(30) Foreign Application Priority Data

Nov. 20, 2015 (DE) ........................ 10 2015 222 955

(51) Int. Cl.
| | | |
|---|---|---|
| *A61N 5/00* | (2006.01) | |
| *A61N 5/10* | (2006.01) | |
| *G06F 16/51* | (2019.01) | |
| *G06F 16/58* | (2019.01) | |
| *G06T 7/00* | (2017.01) | |
| *A61B 6/00* | (2006.01) | |
| *A61B 6/03* | (2006.01) | |

(52) U.S. Cl.
CPC ............ *A61N 5/103* (2013.01); *G06F 16/51* (2019.01); *G06F 16/5866* (2019.01); *G06T 7/0014* (2013.01); *A61B 6/032* (2013.01); *A61B 6/465* (2013.01); *A61B 6/5205* (2013.01); *A61B 6/5217* (2013.01); *A61N 2005/1041* (2013.01); *G06T 2207/10081* (2013.01)

(58) Field of Classification Search
CPC ..................................................... A61N 5/103
See application file for complete search history.

(56) References Cited

U.S. PATENT DOCUMENTS

| | | | |
|---|---|---|---|
| 2008/0253518 A1* | 10/2008 | Foshee ................. | A61N 5/103 378/65 |
| 2013/0150647 A1 | 6/2013 | Chen et al. | |
| 2015/0103969 A1 | 4/2015 | Flohr et al. | |

FOREIGN PATENT DOCUMENTS

CN        104036109 A        9/2014

* cited by examiner

*Primary Examiner* — Dani Fox
(74) *Attorney, Agent, or Firm* — Schiff Hardin LLP

(57) ABSTRACT

A contouring processor transmits contour data to a radiotherapy device, and uses a key generated by a key generator, which identifies a target volume to be irradiated. The contouring processor is designed to access a contour database in order to acquire reference contour data in reference images relating to the target volume for determining the contour data. The contouring processor has a calculation processor designed to calculate volume percentiles from the acquired reference contour data and to emit them on a user interface to determine the contour data.

16 Claims, 3 Drawing Sheets

METHOD AND COMPUTER USING CONTOUR DETERMINATION FOR CONFIGURING A RADIOTHERAPY APPARATUS

BACKGROUND OF THE INVENTION

Field of the Invention

The present invention concerns a contouring processor, a method and a radiotherapy apparatus as well as a storage medium encoded with programming instructions for acquiring contour data to determine a target volume for configuring a radiotherapy apparatus, such as a particle generator.

Description of the Prior Art

Linear accelerators are used, among other things, in radiation therapy for treating tissue, particularly tumor diseases. Here charged particles are usually accelerated to high energies, formed into a particle beam and fed via a high energy beam transporting system to one or more radiotherapy devices. The target volume to be irradiated is then irradiated using the particle beam of one of these radiotherapy machines.

Before the linear accelerator or another radiotherapy device can be put into operation, it must first be configured, among other things, as to which target volume is to be irradiated. For this purpose, a computed tomography (CT) scan of the relevant region of the patient is generally performed in advance. The cross-sectional images thus obtained are transmitted via a network to a computer. The contours of the regions to be irradiated are marked on these cross-sectional images, as well as organs at risk such as the spinal canal, liver, kidneys, lenses in the eyes, etc.

The contoured cross-sectional images or volumes can be displayed in a two-dimensional or three-dimensional manner. The contoured regions are then assigned a target dose value that is selected such that the tumor tissue is irradiated as fully as possible and healthy surrounding tissue is damaged as little as possible. Contour data containing instruction sets is then calculated from the contour-enhanced cross-sectional images and transmitted by a planning system having a device configuration computer for the radiotherapy device. Conventionally, the doctor or technician at the device configuration computer has been tasked with determining an optimum irradiation technique, i.e. the number of fields, their size, shape and incident beam angle, and with determining the resulting dose distribution in the patient. Computer-based systems assist with this task, e.g. by the use of a beam-based display (beam's eye view). The basic goal is to irradiate the tumor as homogeneously and adequately as possible while causing minimum damage to the organs at risk and surrounding healthy tissue. The accelerator, or more specifically the radiotherapy device then performs the irradiation in a downstream time phase or later.

In the prior art, it is known to compare a large number of dose volume histograms and use this as a basis for calculating the respective target dose. However, the user receives no indications for contouring.

In addition, contouring tools are known that suggest contours, particularly for organs at risk, on the basis of landmarks. However, landmark-based contouring tools are unsuitable for contouring (tumor) tissue to be irradiated and therefore for determining the target volume (even though they can indeed be additionally used as aids for defining the position of the organs at risk). This is because the site of tumor tissue is generally not landmark-dependent (and has no particular distance from the spinal column, bones or an easily identifiable organ).

Contour data have conventionally been entered locally on-site and without matching that data with other (external) data sources, and manually by the doctor. This has a high potential for error. It is obvious that incorrect contour data has unacceptable consequences, as in some circumstances too much healthy or too little malignant tissue will be irradiated.

SUMMARY OF THE INVENTION

Proceeding from the aforementioned prior art, an object of the present invention is to automate and improve the configuring of a radiotherapy device and make the configuration less error-prone. In addition, the configuration process should be accelerated.

The object is achieved according to a first aspect of the invention by a contouring processor for transmitting instruction sets with contour data to a radiotherapy device, wherein the contouring processor is designed to access a contour database using a key generated by a key database, and to identify a target volume to be irradiated (e.g. entered via a graphical user interface) in order to acquire reference contour data in reference images relating to the target volume. The reference contour data are used to determine the contour that defines or rather delimits the target volume.

Contour data are then generated from the contour. The contour per se is not transmitted to the radiotherapy device, but only the contour data calculated therefrom. The contour data include control commands for configuring the radiotherapy device that are transmitted thereto for this purpose. The contour data can be read in by a control program e.g. for a linear accelerator. The contour data basically contain a sequence of control commands (e.g. collimator open/closed, rotate, etc. . . . ).

According to the invention, reference images in which the same target volume is at least partially represented are identified in the contour database. In a definition phase, further correlation criteria (between image, or rather the target volume represented in the image, and reference image) are defined (e.g. across particular attributes). This advantageously enables the search for reference images to be tailored very specifically to the respective application.

The contouring processor can be incorporated into a planning system or more precisely into a device configuration computer and is used to configure the radiotherapy device or more precisely the linear accelerator. The contouring processor can also be provided as a separate computer-based module, e.g. as a software tool and/or as a hardware tool.

In this context, the term "configuration" means technical settings of the linear accelerator, such as field delimiting by diaphragms, i.e. collimators (e.g. by means of irregular field diaphragms—multileaf collimator). In addition, configuration can relate to settings for gating in the case of breath-dependent irradiation, in particular time windows (e.g. during expiration only) or configurations for breath-hold procedures, the determining of an accelerator voltage and/or of isodose curves and the calculating of integral doses, etc. The accelerator is configured on the basis of the contour data and the dose data. For this purpose, the contour data include specific instruction sets that are transmitted directly to the radiotherapy device where they are executed.

The target volume is usually malignant tumor tissue which is to be selectively irradiated. It can be in an organ or extend beyond organ boundaries or only relate to part of an organ. Surrounding organs at risk or healthy tissue shall be undamaged by the irradiation as far as possible. The target volume is currently defined in an image-aided manner by placing a contour around the target volume.

According to the invention, a contour can be considered and applied in different specific forms, in particular as:
GTV, gross tumor volume
CTV, clinical target volume
PTV, planning target volume
TV, target volume—treated volume
IV, irradiated volume.

Depending on the medical circumstances, different tumor-specific margins are added as a safety clearance (e.g. 1 cm margin, etc.) which must be taken into account for the irradiation. In the present invention, this can be taken into account by applying the different specific forms of the contours.

The image data and the reference image data are two-dimensional, three- or multi-dimensional data sets and can be read in e.g. from a PACS system (picture archiving and communication system).

The contouring processor according to the invention is therefore used to check and verify an intended contouring and can increase the safety of the device.

In an embodiment of the invention, the contouring processor has a calculation processor designed to calculate volume percentiles from the acquired contour data and provide them for display on a monitor.

According to another aspect, the object of the invention is achieved by a system designed to generate an instruction data set for configuring a radiotherapy device. In particular, the beam guidance of the radiotherapy device onto the target volume shall be configured. The system has:
An interface (in particular a data interface) to the radiotherapy device via which the contour data can be read in. The contour data comprises instruction sets for controlling the radiotherapy device and in particular for beam guidance of the radiotherapy device onto the target volume.
A contour database in which a set of contour reference images with respective reference contour data is stored, wherein the database tuples are indicated or tagged over the target volume shown in the respective reference image.
A contouring processor as described above.

The contour database is preferably a relational database in which the image data and contour data and any metadata (contouring by doctor XYZ, at time ABC, etc.) is stored in an anonymized manner in order to protect the identity of the patient or doctor or other sensitive data.

In a preferred embodiment of the invention, the system additionally comprises a user interface which can be implemented as a monitor. On the user interface, a window can be displayed in which the acquired reference contour data and an intended contour are indicated simultaneously and in particular in superimposed form.

Predeterminable volume percentiles relating to the sample space of the acquired reference contour data are preferably calculated. Preferably, only the volume percentiles and an intended contour are shown simultaneously on the user interface. This enables the user to recheck and possibly verify his or her intended contour on the basis of the reference contours displayed.

In order to increase the safety of the radiotherapy planning system, it is advantageously provided that the system additionally comprises a warning device which is designed to issue a warning signal if it has been detected—particularly by a processing unit—that an intended contour differs from a reference contour by a predefinable threshold value.

For example, in a definition phase preceding execution, the 5% and 95% percentiles are set as threshold values. Therefore, as soon as the intended contour lies outside the 95% volume percentile or inside the 5% volume percentile, an audible and/or visual and/or other warning signal (e.g. indication as pop-up window) is generated and output. These threshold values can also be made more flexible, e.g. it can be "permitted" that 1% of the target volume may lie within the 5% percentiles or outside the 95% percentiles.

According to another aspect, the object is achieved by a method for determining a contour for a target volume. From the determined contour, contour data with control commands for configuring a radiotherapy device is then calculated. The method includes:
Acquiring attributes for the respective target volume;
Calculating a key identifying the target volume on the basis of the attributes acquired;
Accessing a contour database using the calculated key to search for a set of reference images with reference contour data, wherein the target volume is represented in the reference images;
Emitting the reference contour data on a user interface to determine the contour data.

The key identifying the target volume is preferably calculated from one of the following attributes:
Site of the target volume, i.e. of a tumor to be irradiated and/or
TNM classification of the tumor and/or
Size of the tumor and/or
Staging or the tumor and, associated therewith, information concerning its spread and/or
Grading of a tumor and, associated therewith, information concerning the malignity of the tumor and/or
Histological and/or microscopic data sets concerning the type of tumor.
Molecular markers of the tumor, e.g. the presence of specific receptors (e.g. HER2, EGFR) or the expression of particular genes in the tumor In a preferred embodiment of the invention, a set of reference images is stored in the contour database for each identifying key, so that contour verification can be performed on the basis of a large number of reference contours in reference images.

In another embodiment the invention, for each reference image from the set of reference images relating to the target volume that are available in the reference database, a predefinable number (e.g. three) and a predefinable type (5%, 50%, 95%) of volume percentiles is calculated and output. Preferably the number and/or type of the percentiles to be calculated can be efficiently preset via a slider.

In a preferred embodiment of the invention, the contour that is to be acquired as the reference contour in each case can also be set in the definition phase:
a GTV contour (for a gross tumor volume),
a CTV contour (for a clinical target volume),
a PTV contour (for a planning target volume),
a TV contour (for a treated volume)
an IV contour (for the target volume to be actually irradiated).

In the above list, the first contour listed is encompassed by the second contour in each case. A number of the above-mentioned contours can also be selected. The volume percentiles can be calculated and displayed for one or more of the aforementioned contours. The presetting can therefore also include the specific form of the contour. Thus in the preceding definition phase, it can be determined that e.g. the IV contour is to be calculated in addition to the GTV contour. Then the associated reference contours are also acquired accordingly in the corresponding specific form (GTV, IV).

In another embodiment of the invention, an intended contour is shown with at least one calculated volume percentile of the reference contour—in a corresponding specific form—in a common screen display.

In another embodiment of the invention, an anatomical atlas of reference images with their respective attributes and their respective reference contour data is stored in the contour database, wherein the reference images are indicated or rather tagged above the target volume represented therein.

In another embodiment of the invention, the reference images and/or the reference contour data are elastically registered in the contour database in order to allow an efficient assignment in the medical context so that, among other things, local distortions in the images or contours (e.g. due to different viewing angle, shapes, positions of the tumor in the tissue) can be taken into account. In addition, the elastic registration allows matching to the patient anatomy.

According to another aspect, the object is achieved by a non-transitory, computer-readable data storage medium encoded with program code that is suitable for carrying out the above described method when the executed in a computer.

The different embodiments described above are applicable to all of the aspects of the invention. The functional features of the method are implemented by corresponding modules, in particular hardware modules or microprocessor modules, in the apparatus, and the system. It is likewise within the scope of the invention to combine the above-mentioned different embodiments or further developments of the invention.

DESCRIPTION OF THE PREFERRED EMBODIMENTS

Figure 1:
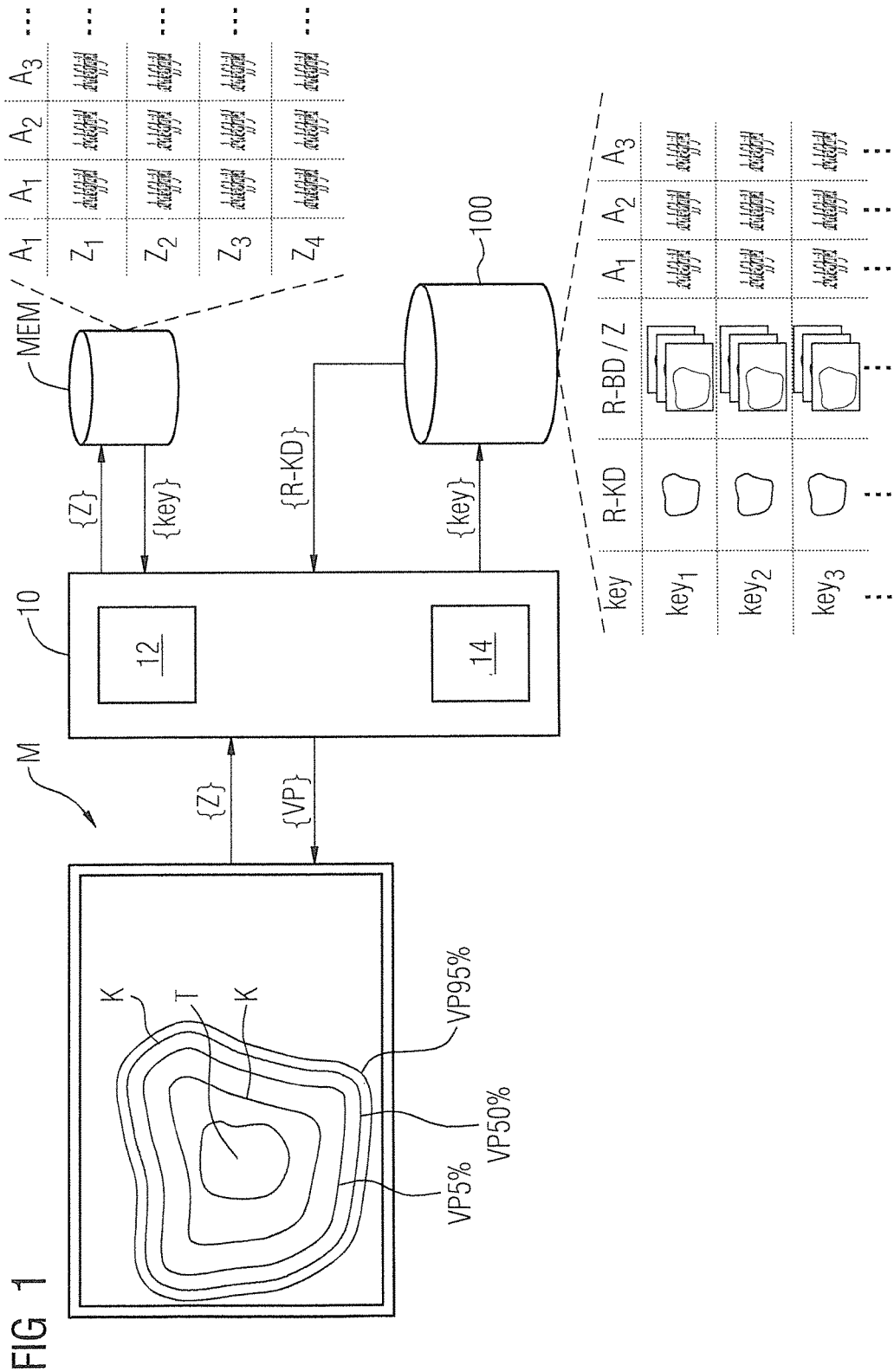
FIG. 1 shows a schematic overview of a system according to a preferred embodiment of the invention.

FIG. 1 shows a contouring processor 10 as the central instance of the inventive system for determining a contour K for a target volume Z. From the determined contour K—particularly on a planning computer—contour data KD for an object to be irradiated using a radiotherapy device 1000 or for the target volume Z can then be automatically determined, said data comprising control commands for configuring the radiotherapy device 1000. From the contours K, the planning system creates a radiotherapy treatment plan that is transmitted to the radiotherapy device 1000 or more precisely to the linear accelerator. This radiotherapy treatment plan contains control instructions and commands (e.g. commands for setting the irradiation angle, dose values, travel paths of the gantry, for adjusting the collimator leaves, etc.).

The quality of the underlying data, particularly of the contour data KD and the contour K, is critically important for optimum adjustment of the device.

Prior to irradiation by the radiotherapy device 1000, which can be implemented as a linear accelerator, telecobalt machine, particle therapy device (proton- or heavy-ion-based) or as a device using nonionizing radiation, it is necessary to determine the target volume Z to be irradiated via contour data KD in order to configure the device accordingly. The method according to the invention is designed to assist the doctor by searching for, acquiring and emitting reference contour data R-KD which is used for verification of an intended contour K. Comparison of the intended contour K in the specific application with reference contours R-KD in similarly positioned cases shall be made possible. It is also possible for volume percentiles to be calculated from the acquired reference contours R-KD and displayed.

The reference contours R-KD are contours that have been created by the same or another user in earlier cases or in other reference images R-BD. The cases (images and their contours) shall have as close a correlation as possible; in particular, the same or a similar target volume Z shall be involved and represented in the image, and preferably the same organ. In addition, it is possible to specify yet more criteria for defining the correlation or rather searching for suitable reference images R-BD. These criteria can be based on at least one of the following attributes A, such as site of the tumor, also location in the respective organ, classification according to a TMN classification, the type of diagnosis, in particular according to ICD 9 or 10, the degree of spread or metastasis, i.e. staging, e.g. a T-Stage, malignancy or grading of the tumor as information as to how differentiated the tumor tissue is, a tumor type and/or other histological, microscopic and/or medical metadata.

The goal is to find reference images R-BD that correlate as closely as possible with the current image to be contoured or more precisely the target volume Z represented therein in order to use the reference contours R-KD in the reference images R-BD for the comparative calculation. In addition, different volume percentiles shall be calculated from the contoured reference images R-BD in order to allow statistical assessments, e.g. that the volume defined by the reference contour R-KD has been encompassed by 5%, 50% or 95% of all the provided cases of reference contours R-KD. This enables the currently intended contouring for configuring the linear accelerator to be verified.

As shown in FIG. 1, the contouring processor 10 has a key generator 12 and a calculation processor 14. The key generator 12 is configured to acquire or calculate a key for unambiguously identifying reference images R-BD which are stored in a central server or in a database 100. In one embodiment of the invention, the key can be used in particular for database access to database tuples Tp. The key is generated for a target volume Z which is to be irradiated. The key is preferably calculated from one or more attributes A. The attributes A can be the factors explained above for defining a correlation between image and reference image. An attribute A can be the site of a tumor, the size of a tumor and/or its spread, etc. The associated values of the attributes A can be stored in a key database or in a memory MEM preferably operating as a server which is accessed by the key generator 12. The contouring processor 10 uses this key to access the contour database 100 to search for reference contour data R-KD in reference images R-BD in which the same target volume Z is represented. These can be the same or another patient's images in which the same tumor having the same specifications (in respect of the above-mentioned attributes such as site, spread, etc.) has been contoured. The reference contouring R-KD may have been carried out by the same or different users (doctors). Through the accessing of the contour database 100 using the key, a set of reference contour data R-KD will (generally) be found which is sent to the calculation processor 14 as the search result. The calculation processor 14 now calculates for the reference contour data R-KD a predeterminable type and number of volume percentiles, in particular a 5%, 50% and 95% percentile. According to the invention, not all the found reference contour data R-KD is therefore output and displayed on the monitor M, as this would no longer be displayable in an easy-to-view form because of the large number of contours, but only a predeterminable number of volume percentiles of the found set of reference contour data R-KD. Therefore, only a selection of the found set with additional statistical information is displayed, which allows rapid further processing on the planning system.

The volume percentiles VP of the found set that are calculated according to predefinable conditions can be represented in graphical format and forwarded to a monitor M for display. Usually the contour K intended by the user is shown on a screen display together with the calculated volume percentiles VP of the set of reference contour data R-KD so that, at a glance, the user obtains an overview of how other users would have determined the respective contour K for this target volume Z and these forms of tumor.

Using the display, the user can once again partially, i.e. in certain areas, or completely verify, change or adapt the contour originally intended by him in order to finally determine the contour data KD. The thus determined contour data KD with corresponding control commands is then used to configure the linear accelerator 1000.

The contour database 100 can be a relational database which is structured in a plurality of tables and wherein a key in each case identifies a tuple Tp relating to a particular target volume Z. A target volume Z can therefore be assigned to a plurality of reference images R-BD in the contour database 100. In particular, all the reference images R-BD in which the target volume is at least partially represented is assigned to the target volume Z. The reference images R-BD are all contoured (reference contour data). This reference contour data R-KD are read in for a target volume Z or for a comparable case by the contouring processor 10. The calculation processor 14 calculates the volume percentiles VP from the read-in reference contour data R-KD (found set of the database access) and displays it on a user interface, in particular a monitor M. After detection of a verification signal by the user, the contouring processor 10 then transmits the determined and verified contour data KD to the linear accelerator 1000 for configuration.

Figure 3:
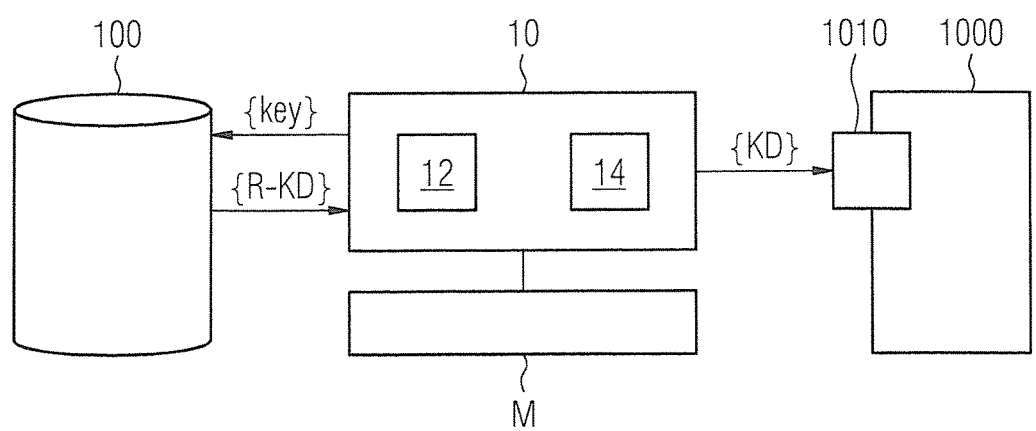
FIG. 3 is a block diagram of a system having a contouring processor in an exemplary embodiment.

FIG. 3 again schematically illustrates the basic setup of the system according to the invention. The contouring processor 10 accesses the contour database 100 in order to determine the reference contour data R-KD in comparable cases, i.e. in cases in which the same target volume Z is also represented. This is forwarded to the calculation processor 14 as the found set. The volume percentiles VP calculated by the calculation processor 14 on the basis of the found set are displayed on the monitor M, and the user can verify or re-modify and thus finally determine his intended contour. The user can also be aided by the system so that the determination takes place automatically or semi-automatically (e.g. by input of indirect commands such as "Match intended contour in region XYZ to reference contour R-KD ABC or to a particular volume percentile"). The determined and verified contour data KD are then forwarded to the planning system which then generates control commands that are read in via an input interface 1010 on the linear accelerator 1000 and used to configure the device 1000.

Figure 2:
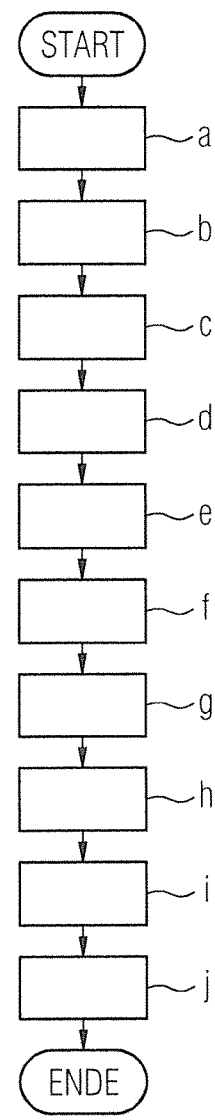
FIG. 2 is a flowchart of a method according to a preferred embodiment of the invention.

FIG. 2 shows a flowchart according to a preferred embodiment of the invention. After the start of the method, in step a, the attributes A for the target volume Z to be irradiated are acquired. In step b, the key is calculated from the acquired attributes A. In step c, the contour database 100 is accessed. Alternatively, the contour database can also be implemented as a server having an appropriately designed interface for data access. In step d, by use of the key, the set of reference images R-BD in which the respective target volume Z is represented and which are enhanced with reference contour data R-KD is searched for. In step e, the reference contour data R-KD is output and then, in step f, displayed on the monitor M preferably together with the intended contour data KD.

In a preferred further embodiment of the invention, volume percentiles VP which are emitted preferably graphically in a differentially coded manner (e.g. in terms of color or graphically) on an interface (e.g. monitor M) can be calculated from the found set of reference contour data R-KD. The combined displaying of the intended contour K and the volume percentiles VP of the reference contour data R-KD takes place in step h. In step i, the contour data KD is determined and sent to the radiotherapy device 1000 for configuration. This terminates the method.

Figure 4:
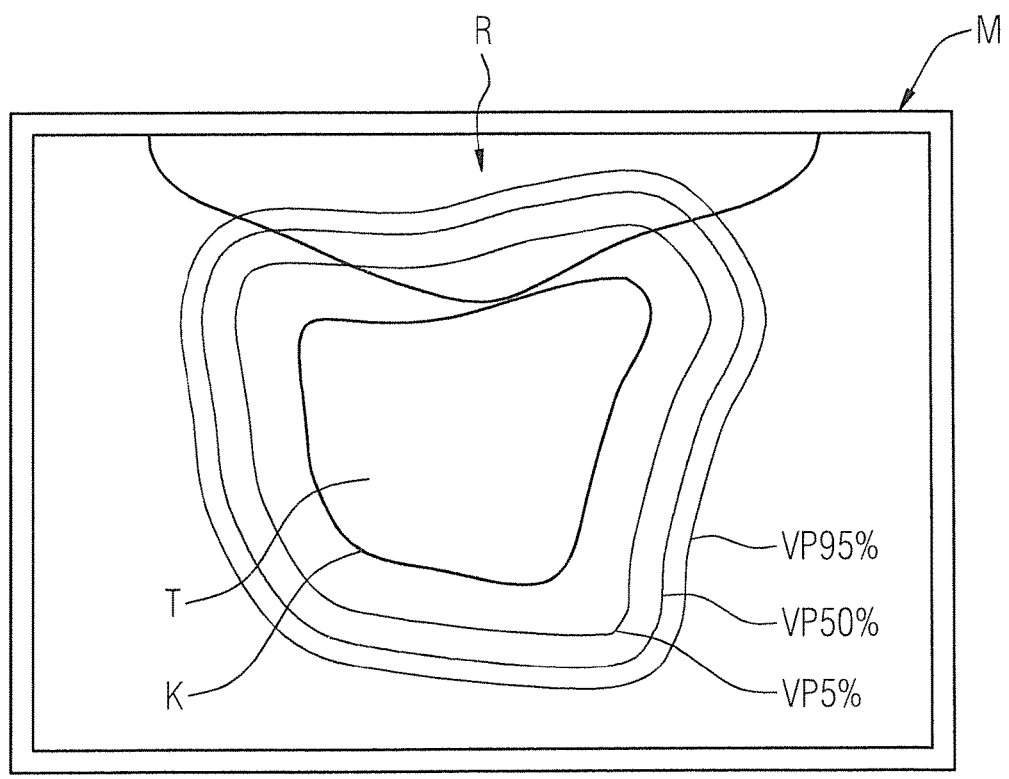
FIG. 4 shows a display of a number of volume percentiles of reference contour data on a monitor.

FIG. 4 shows an example of the merged display on the monitor M with three volume percentiles VP of the reference contour data R-KD. In this example, the reference contour data R-KD is displayed in the form of three different, calculated volume percentiles (here: 5%, 50% and 95%). This means that the respective volume is included in 5%, 50% and 95% of the contoured images for the respective tumor T having the respective attributes A (i.e. characterizing values). In other embodiments, other percentiles or even fewer or additional percentiles can be calculated and displayed here. The percentiles are preferably inserted directly into the display of the contour K, preferably by superimposition. As shown in FIG. 4, the found set with the reference contour data R-KD is not displayed directly, but only after a further calculation, namely the calculation of the percentiles VP. The advantage of this is that the user is only faced with the necessary information and does not need to view the multiplicity of found reference contours R-KD.

In addition to the instruction sets for controlling the radiotherapy device 1000, the contour data KD calculated on the basis of the contour K can also include further metadata, such as e.g. a verification signal which indicates that the contour has been verified by comparison with reference contours R-KD and/or other statistical and/or medical data.

As schematically illustrated in FIG. 4, an organ at risk R (also termed OAR) which, if possible, must not be irradiated is often located close to the target tissue containing the tumor T. For fine delineation of the area to be irradiated with respect to the organ at risk R, the slider can be actuated to define the volume percentiles VP and/or another slider to define the specific forms of the contour in order to change the different specific forms of the contour K and the volume percentiles VP thereof and therefore the calculation.

In another embodiment of the invention, the regions of the intended contour K which lie outside the 90% band can be highlighted (e.g. using color). Other pre-settings in respect of the percentiles are possible at any time.

The invention offers a number of advantages compared to existing techniques. For example, the radiotherapy device can be put into operation much more quickly, as the configuration times can be reduced. In addition, the radiotherapy device can be configured much more safely in that incorrect manual contourings can be prevented by automatic comparison with reference contours. The system can also be implemented as a self-learning system by feeding new or newly verified contours into the database 1000 for future cases.

It should be noted that the description of the invention and the exemplary embodiments must essentially be understood as being non-limiting in respect of the particular physical implementation of the invention. All the features explained and indicated in connection with individual embodiments of the invention can be provided in different combinations in the subject matter according to the invention in order to implement their advantageous effects simultaneously. It will be apparent to those skilled in the art that the invention can be used not only for linear accelerators and also for other radiotherapy devices which have to be configured. Moreover, the components of the contouring processor of the system can be implemented in a distributed manner over a number of physical products.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A contouring computer for a radiotherapy device, said contouring computer comprising:
   a processor;
   an input interface to said processor that receives an input that electronically represents at least one attribute that describes a target volume to be irradiated by said radiotherapy device;
   said processor comprising a key generator configured to generate an electronic key from said at least one attribute, said electronic key identifying said target volume;
   said processor being configured to access a contour database of reference images respectively of different target volumes and to use said electronic key to select reference contour data from at least one of said reference images that contains a reference image target volume corresponding to the target volume identified by said electronic key, the selected reference contour data defining a contour of the reference image target volume that corresponds to the target volume identified by said electronic key; and
   said processor being configured to generate and emit an electronic output that represents said contour data.

2. A contouring computer as claimed in claim 1 comprising:
   a display monitor in communication with said processor;
   said processor being configured to display, at said display monitor, an image of said reference image target volume with a contour conforming to said reference contour data; and
   said processor being configured to calculate a plurality of different volume percentiles of said reference image target volume and to display the calculated different volume percentiles on said display monitor in said reference image target volume.

3. A system for determining contour data for a target volume for configuring a radiotherapy device, said system comprising:
   a contour database of reference images respectively of different target volumes, each reference image containing a reference image target volume and being associated with contour data for a contour of said reference image target volume;
   a processor;
   an input interface to said processor that receives an input that electronically represents at least one attribute that describes a target volume to be irradiated by said radiotherapy device;
   said processor comprising a key generator configured to generate an electronic key from said at least one attribute, said electronic key identifying said target volume;
   said processor being configured to access said contour database and, using said electronic key, to select at least one set of reference contour data from at least one of said reference images that contains a reference image target volume corresponding to the target volume identified by said electronic key; and
   said processor being configured to generate and emit an electronic output that represents said contour data of the contour of the reference image target volume corresponding to the target volume identified by said key.

4. A system as claimed in claim 3 comprising a display monitor forming a user interface that allows a user to enter intended contour data for said target volume into said processor, and wherein said processor is configured to display said contour data for said reference image target volume and said intended contour data simultaneously.

5. A system as claimed in claim 3 wherein said processor is configured to calculate volume percentiles for each of said reference contour data and said intended contour that are simultaneously displayed on said display monitor.

6. A system as claimed in claim 3 wherein said processor is configured to emit a humanly perceptible warning if said processor detects that said intended contour differs from said reference contour by a predetermined threshold amount.

7. A method for determining contour data for target volume for configuring a radiotherapy device, said method comprising:
   providing an input to a processor that electronically represents at least one attribute that describes a target volume to be irradiated by said radiotherapy device;
   in said processor, generating an electronic key from said at least one attribute, said electronic key identifying said target volume;
   from said processor, accessing a contour database of reference images respectively of different target volumes and to use said electronic key to select reference contour data from at least one of said reference images that contains a reference image target volume corresponding to the target volume identified by said electronic key, the selected reference contour data defining a contour of the reference image target volume that corresponds to the target volume identified by said electronic key; and
   in said processor, generating and emitting an electronic output that represents said contour data.

8. A method as claimed in claim 7 comprising receiving, as said attribute to said processor, an attribute selected from the group consisting of a site of a tumor, TNM classification of a tumor, a size of a tumor, staging of a tumor, grading of a tumor, histological data sets relating to a tumor type, microscopic data sets relating to a tumor type, and molecular information concerning a tumor.

9. A method as claimed in claim 7 comprising storing a set of said reference images in said contour database for each key.

10. A method as claimed in claim 7 comprising, in said processor, calculating a predetermined number and type of volume percentiles from said reference contour data for each reference image target volume in said contour database.

11. A method as claimed in claim 7 comprising calculating said percentiles via a slider entered into said processor via said input interface.

12. A method as claimed in claim 7 comprising displaying an intended contour at a display monitor in communication with said processor with at least one calculated volume percentage of all contours of respective reference image target volumes in said contour database.

13. A method as claimed in claim 7 comprising storing an anatomical atlas of said reference images and respective attributes associated therewith and respective reference contour data associated therewith in said contour database.

14. A method as claimed in claim 7 comprising elastically storing said reference images in said contour database.

15. A method as claimed in claim 7 comprising elastically storing said reference contour data in said contour database.

16. A non-transitory, computer-readable data storage medium encoded with programming instructions, said storage medium being loaded into a contouring computer for configuring a radiotherapy device, and said programming instructions causing said contouring computer to:

receive an input that electronically represents at least one attribute that describes a target volume to be irradiated by said radiotherapy device;

generate an electronic key from said at least one attribute, said electronic key identifying said target volume;

access a contour database of reference images respectively of different target volumes and to use said electronic key to select reference contour data from at least one of said reference images that contains a reference image target volume corresponding to the target volume identified by said electronic key, the selected reference contour data defining a contour of the reference image target volume that corresponds to the target volume identified by said electronic key; and generate and emit an electronic output that represents said contour data.

* * * * *